United States Patent [19]

Trubiano

[11] 4,369,308

[45] Jan. 18, 1983

[54] LOW SWELLING STARCHES AS TABLET DISINTEGRANTS

[75] Inventor: Paolo C. Trubiano, Somerville, N.J.

[73] Assignee: National Starch and Chemical Corporation, Bridgewater, N.J.

[21] Appl. No.: 286,411

[22] Filed: Jul. 24, 1981

[51] Int. Cl.$^3$ ............... A61K 47/00; C13L 1/00; C08B 31/00
[52] U.S. Cl. ................... 536/106; 106/210; 106/213; 424/361; 426/578
[58] Field of Search ........... 426/578; 106/210, 213; 424/361; 536/102, 106

[56] References Cited

U.S. PATENT DOCUMENTS

| | | | |
|---|---|---|---|
| 2,884,412 | 4/1959 | Neukom | 106/210 |
| 3,034,911 | 5/1962 | McKee et al. | 106/210 |
| 3,181,998 | 5/1965 | Kanig | 167/82 |
| 3,293,132 | 12/1966 | Stoyle et al. | 167/82 |
| 3,490,742 | 1/1970 | Nichols et al. | 252/99 |
| 3,584,114 | 6/1971 | Cavalli et al. | 424/38 |
| 3,622,677 | 11/1971 | Short et al. | 424/361 |
| 3,725,556 | 4/1973 | Hanssen et al. | 424/357 |
| 4,072,535 | 2/1978 | Short et al. | 106/210 |
| 4,104,212 | 8/1978 | Bruner | 260/17.3 |
| 4,104,213 | 8/1978 | Chiang et al. | 260/17.3 |
| 4,183,969 | 1/1980 | Rubens | 426/578 |
| 4,207,355 | 6/1980 | Chiu et al. | 426/578 |
| 4,219,646 | 8/1980 | Rubens | 536/109 |
| 4,228,199 | 10/1980 | Chiu et al. | 426/578 |
| 4,229,489 | 10/1980 | Chiu et al. | 426/578 |
| 4,281,111 | 7/1981 | Hunt et al. | 426/578 |
| 4,303,451 | 12/1981 | Seidel et al. | 426/578 |

FOREIGN PATENT DOCUMENTS

| | | | |
|---|---|---|---|
| 2062459 | 5/1981 | United Kingdom | 536/102 |
| 2078767 | 1/1982 | United Kingdom | 536/102 |

*Primary Examiner*—Ronald W. Griffin
*Attorney, Agent, or Firm*—Edwin M. Szala; Margaret B. Kelley

[57] ABSTRACT

Starches useful as tablet disintegrants consist essentially of a free-flowing, crosslinked and pregelatinized starch powder having a moisture content of about 12% by weight or less. The starch is characterized by its uniformly swollen, virtually non-birefringent granules, by a swelling value in cold water of above 3 ml. and below 25 ml., and by an acid viscosity breakdown of 400 B.U. or less, all of which are correlated to this disintegration performance. The better starch disintegrants (i.e. the more highly crosslinked) have swelling values of 18 ml. or less and show little or no breakdown (0–150 B.U.). The modified starches may be used in any tabletting method (e.g. direct compression or granulation), typically in amounts of about 10% by weight or less.

12 Claims, No Drawings

LOW SWELLING STARCHES AS TABLET DISINTEGRANTS

BACKGROUND OF THE INVENTION

This invention relates to low swelling starches suitable for use as tablet disintegrants. It also relates to a method for preparing and characterizing suitable starch powders. It further relates to compressed tablets containing the starch disintegrants and to methods for preparing the tablets by wet granulation, dry granulation, or direct compression.

Tablets usually consist of several inert materials, referred to as excipients, in addition to the active ingredient which is present in amounts sufficient to accomplish the desired pharmaceutical, nutritive, or chemical effect. These excipients are generally classified according to their function, such as diluents (also called bulking agents and fillers), binders which hold the ingredients together, disintegrants which help the tablet to break apart when placed in a fluid environment and thus release the active ingredient, and lubricants to improve the release of the compressed tablet from the die and punches. In addition, the tablets may contain other substances intended to improve the tabletting process. For example, glidants are added to improve the flow and anti-adhesives are added to prevent film formation on the punches. Other optional ingredients may be dyes, flavors, sweeteners, and antioxidants.

The disintegrants are added directly to the dry ingredients when the direct compression tabletting method is used. When the dry or wet granulation tabletting methods are used, the disintegrant may be added before granulation (intragranularly), after granulation (extragranularly), or part may be added intragranularly and part added extrangranulary.

The disintegrants currently used include native starches, modified starches, gums, cellulose derivatives, microcrystalline cellulose, alginates, clays, effervescent mixtures, and enzymes. Of these, the starches, despite some drawbacks, are the formulator's first choice.

Starch as a disintegrant should not be confused with starch as a binder or diluent since different properties are required for each use. Moreover, the properties required in a disintegrant may depend upon the tabletting method used.

The unmodified native starches which are useful as diluents are not very effective when used as disintegrants unless used at high levels (i.e. 10–20%). They swell only very slightly when exposed to water at the temperature found in gastric or intestinal juices. This results in a slight increase in volume which eventually weakens the forces holding the tablet together and thus breaks it apart.

The cooked non-granular starches which are satisfactory as binders are not satisfactory as disintegrants. They can be cooked and added as a paste or gelatinized by drum drying (drum dried starches are often referred to as pregelatinized starches). The cooked or gelatinized starches do not readily disperse; they tend to hydrate rapidly and in many cases form a tacky film on the tablet's surface, thus preventing water penetration into the tablet to aid in disintegration.

Various attempts have been made to modify the cold-water-swelling characteristics of starches to improve their disintegration properties. These have included chemical and physical modification of the starch. Chemical derivatization has produced cold-water-swelling, cold-water-soluble intact granular starches such as starch phosphate, starch sulfate, and carboxymethyl starch (see U.S. Pat. No. 3,034,911 issued May 15, 1962 to I. K. McKee et al.). Physical modification by compaction, with or without the use of supplemental thermal energy, has produced partially cold-water-swelling, cold-water-soluble starches which are claimed to be useful as binder-disintegrants for direct compression tabletting (see respectively U.S. Pat. Nos. 3,622,677 and 4,072,535 issued Nov. 23, 1971 and Feb. 7, 1978 to R. W. P. Short et al.). This physical modification disrupts the granular structure and results in a mixture of birefringent and non-birefringent granules, some aggregates of birefringent and non-birefringent granules and fragments, as well as completely solubilized starch.

It is an object of this invention to provide modified starches which are low swelling in cold water and which are suitable for use as disintegrants in compressed tablets prepared by any tabletting method.

SUMMARY OF THE INVENTION

The above object is achieved by crosslinking and pregelatinizing, in the presence of water, a cold-water-insoluble, granular starch, drying the crosslinked, pregelatinized starch if necessary, and then pulverizing the dry starch so as to provide a white, free-flowing starch powder. This modified starch powder is virtually free of birefringent granules, in both the dry state as well as in aqueous dispersions, since all of the granules have been uniformly and partially swollen during the pregelatinization. This controlled swelling during pregelatinization is made possible by treating the base starch with relatively high levels of crosslinking agents. Suitable modified starch powders are characterized by their non-birefringent nature, by their low swelling in cold water, and by a maximum acid viscosity breakdown, all of which are correlated to their disintegration performance. They should have swelling values above about 3 ml. and below about 25 ml. and a breakdown (defined as the loss from peak viscosity with time) of 400 B.U. or less. The Brabender procedure and swelling test will be described hereafter.

The modified starch powders show rapid disintegration times in tablets prepared by both wet granulation and direct compression. This rapid disintegration is believed to stem from the advantageous characteristics of the modified starch powders, particularly the dual action of controlled low swelling combined with "wicking" (i.e. capillary) ability. The novel disintegrants do not swell to the same degree as conventional gelatinized starch powders which, if used as disintegrants, would swell too rapidly and form a gelatinous mass or sheath on the peripheral area of the tablet which then acts as a barrier and prevents further water absorption by the tablet. The modified starch powders swell enough to bring about a significant increase in the volume of the tablets without, however, blocking the porous structure of the tablet or themselves losing their wicking ability. The concurrent increase in volume and continued capillary action of the disintegrants exert a tremendous force within the tablet and effect rapid disintegration.

Compressed tablets containing the modified starch powders also contain an active ingredient, a binder, preferably a lubricant, and optionally a diluent. They may be prepared by any of the conventional tabletting methods. In addition to their excellent disintegration times, the tablets show good hardness and satisfactory storage stability.

DESCRIPTION OF THE PREFERRED EMBODIMENTS

Starch bases suitable for use in preparing the starch disintegrants herein may be derived from any plant source including corn, potato, sweet potato, wheat, rice, sago, tapioca, waxy maize, sorghum, high amylose corn, and the like. Also included are the conversion products derived from any of the latter bases including, for example dextrins prepared by the hydrolytic action of acid and/or heat; oxidized starches prepared by treatment with oxidants such as sodium hypochlorite; fluidity or thin-boiling starches prepared by enzyme conversion or mild acid hydrolysis; and derivatized starches such as ethers and esters. The starch base should be a substantially granular starch.

In the preparation of the modified starch, the starch base is reacted with any crosslinking agent capable of forming linkages between the starch molecules. Typical crosslinking reagents are those approved for use in pharmaceuticals or foods, such as phosphorus oxychloride, soluble metaphosphates, epichlorohydrin, linear dicarboxylic acid anhydrides, adipic-acetic anhydride, and acrolein. However, other known crosslinking agents, such as formaldehyde, cyanuric chloride, diisocyanates, divinyl sulfone and the like, may be used if the tablet will not be ingested, as is the case with laundry detergent and bleach tablets. The preferred crosslinking agents are sodium trimetaphosphate and phosphorus oxychloride.

The crosslinking reaction itself may be carried out according to the standard procedure described in the literature for preparing crosslinked starches (see Chapter 22—"Starch and Its Modifications", pp. 22:26–30 in Handbook of Water-Soluble Gums and Resins, Robert L. Davidson (Ed.), McGraw-Hill Book Co., New York 1980). The exact reaction conditions employed will, of course, depend on the type of crosslinking agent used, as well as the starch base, the reaction scale, etc. The conditions selected should be sufficient to provide highly crosslinked (i.e. low swelling) starches.

It is well known that when native corn starch is pregelatinized by conventional means (i.e. drum drying), most of the granules are completely disrupted because, during the cooking process, the granules reach a maximum degree of swelling and then breakdown under shear or prolonged cooking. When mixing in cold water, the pregelatinized starch swells up and, depending on the source, it may even become thoroughly dispersed. Crosslinked, pregelatinized starches do not breakdown during cooking or under shear since crosslinking toughens the starch granule, inhibits granule swelling, and prevents disruption of the granule during pregelatinization. If the level of crosslinking is properly controlled, it is possible to obtain a modified starch which swells only slightly when mixed with cold water.

The swelling values obtained for various starch bases treated with the same level and type of crosslinking agent vary greatly because the granular size and components (i.e. amylose and amylopectin) also affect swelling during pregelatinization. Hence, it is difficult to characterize the crosslinked, pregelatinized starch powders solely in terms of swelling values. An additional way to characterize suitable starch powders is by an acid Brabender procedure, a procedure commonly used in the food industry to characterize crosslinked, pregelatinized starches. The breakdown in acid viscosity is a measure of the degree of crosslinking and therefore swelling (or viscosity) in water and is correlated with the disintegration performance of the starch powders in the compressed tablets. Thus, the novel starch powders useful as disintegrants herein must have all of the following characteristics—namely, uniformly swollen, virtually non-birefringent granules, a cold water swelling value above 3 and below 25 ml., and an acid viscosity breakdown of 400 B.U. or less. The preferred modified starch powders show little or no breakdown (0–150 B.U.) and have swelling values of 18 ml., preferably 10 ml., or less.

Typically, the crosslinking is carried out by adding the required amount of crosslinking agent to an aqueous starch suspension (about 35–41% solids) at the required temperature (about 20°–50° C.) and pH (about 8–11, depending upon the agent, adjusted with a dilute sodium hydroxide solution). After completion of the reaction, the pH is adjusted to 4.5 to 6 with a dilute mineral acid. The reaction conditions are chosen so as to yield an ungelatinized starch if the pregelatinization step is to be carried out separately.

Preferably, the pregelatinization step is carried out after the crosslinking step; however, it may be carried out simultaneously with the crosslinking and drying step. The latter may be achieved by drum drying an aqueous starch dispersion containing the crosslinking agent (e.g. sodium trimetaphosphate) thus effecting the crosslinking and pregelatinization in situ (see U.S. Pat. No. 4,219,646 issued Aug. 26, 1980 to R. W. Rubens). It may be possible to pregelatinize the native starch first and then reduce the swelling by crosslinking under carefully controlled conditions, such as by means of an organic solvent or water containing high concentrations of salts; however, these methods are usually costly and recovery of the starch is often difficult. Other mechanical means of carrying out the pregelatinization step, e.g. spray drying, flash drying, extrusion, etc., may also be used, if so desired by the practitioner. It should be noted, however, that drum drying is the most economical and efficient and hence preferred.

Sometimes, such as in extrusion, after the crosslinking and pregelatinization step(s), the moisture content of the modified starch may have to be reduced further. For this, typical drying methods can be used such as oven drying, vacuum drying, flash drying, spray drying, and freeze drying. The crosslinked, pregelatinized dry starch should have a moisture content of about 12% by weight or less, preferably about 7–10% or less. Generally the lower the moisture content, the better the performance as a disintegrant.

The modified starch resulting from the drum drying process is in the form of thin, solid sheets which are then pulverized to a particle size compatible with the particle size of the other tabletting components. Preferably, the starch is pulverized to a fine particle size, typically such that at least about 98% passes through a 100 mesh screen (0.0059 in.), at least about 80% passes through a 200 mesh screen (0.0029 in.), and about 35–50% passes through a 325 mesh screen (0.0017 in). The mesh numbers used herein refer to U.S. standard sieves. Usually the finer the particle, the better; however, a very fine particle size is not always desirable. Some very finely pulverized disintegrants, when used with coarse tabletting components, may initially form a homogeneous mixture but will subsequently stratify, thus giving a non-homogeneous mixture. This is the case with all types of disintegrants. Typically, the pulverization step is carried out in a hammer mill such as Raymond, Fitz-mill, or Mikro-Pulverizer.

Compressed tablets containing the modified starch powders as disintegrants may be prepared using any tabletting method, i.e. wet granulation, dry granulation (e.g. slugging), or direct compression [see pp. 318-323 of "The Theory and Practice of Industrial Pharmacy", L. Lachman, H. A. Lieberman, and J. L. Kanig (Eds.), Lea & Febiger, Philadelphia, Pa. 1970 for a discussion of these tabletting methods].

Briefly, the steps involved in a typical wet granulation include mixing the components, preparing the granulating solution, thoroughly mixing the components with the granulating solution to form a dough, coarse screening the moist mass through a sieve, drying the resulting moist granules, screening the dry granules through a sieve, adding the lubricant, and compressing the tablets. The disintegrant may be added intragranularly and/or extragranularly. Other wet granulation methods are also useful herein.

The steps involved in slugging are mixing the powdered components, compressing the mixture into hard slugs, reducing the slugs to granules, screening, adding the disintegrant and lubricant, and compressing the mixture into tablets. If desired, the disintegrant or part of it may be added prior to granulation. Appropriate adjustments of the moisture content may be made, where necessary or desirable, during formulation to improve the tabletting characteristics of the mixture.

The preferred and most economical method, direct compression, requires only two steps—mixing the dry components and compressing the mixture into tablets.

The active ingredients which may be employed in compressed tablets containing the starch disintegrants herein constitute all active ingredients compatible with the modified starch powders and include pharmaceutical active ingredients. The particular nature of the active ingredient is not critical, however, and non-pharmaceutical active ingredients such as pulverized detergents, dyes, pesticides, and foods may also be employed.

The choice of a binding agent depends upon the amount of binding required and the binder's compatibility with the other tabletting components, particularly the active ingredient if it is a drug. For wet granulation, typical binders include natural gums, gelatin, starch pastes, gelatinized starches, and cellulose compounds such as methyl-cellulose and sodium carboxymethyl cellulose. They are wetted either prior to or after mixing with the other tabletting components. Typically, they are wetted with water, but some may be wetted with a suitable solvent. The binders suitable for use in direct compression tabletting are limited. Monobasic, dibasic, and tribasic calcium phosphate salts, various types of lactose, microcrystalline cellulose, compressible sugars, and precompacted starches are often used in this tabletting method.

The amount of active ingredient, binder, and diluent if any, will depend not only on potency desired but also on the compatibility of the components, the tabletting method used, and also the hardness, friability, disintegrability, dissolution, and/or stability of the final tablet. Given the minimum and preferred characteristics desired in the final tablet, the tolerable limits on the weight ratio of the components may be easily determined by the skilled practitioner.

Depending upon the type and contemplated end use of the final tablet and the type of binder used, the amount of disintegrant required may vary over a wide range. Being more effective than standard starches, the novel disintegrants will be used at considerably lower levels, typically at less than 10% by weight, based on the total weight of the tabletting mixture.

Tabletting aids such as lubricants are typically used. Anti-adhesives, glidants, flavors, coloring agents, and the like which are conventionally employed in preparing particular tablets may be used. They are incorporated in the appropriately effective amounts into the compressed tablets herein.

The following examples will more fully illustrate the embodiments of this invention. In the example, all parts are given by weight, all temperatures are in degrees Celsius, and D.B. indicates dry basis.

The following procedures were used to characterize the modified starch powders useful herein as disintegrants and to prepare and evaluate compressed tablets containing these starches as disintegrants.

A. SWELLING TEST

A total of 1.0 g. of starch is mixed with 99.9 mls. of distilled water for 2 minutes in a Waring Blendor set at low speed and then poured into a 100 ml. graduated centrifuge tube and centrifuged for 20 minutes at 2000 R.P.M. The swelling value in milliliters is the volume of the settled hydrated starch. The more crosslinked the starch is, the lower the swelling volume and therefore the lower the viscosity in water.

B. ACID BRABENDER PROCEDURE

Water and glacial acetic acid are placed in the bowl of a Sunbeam Mixmaster, and with the speed set at #1 the starch powder is sprinkled into the bowl over a 2 min. period. The amount of water used should be sufficient to give 460 g. of a dispersion containing 41.4 g. starch powder (anhydrous basis) and 4.6 g. glacial acetic acid. The dispersion is then placed in the cup of a Brabender/Visco/Amylograph (Model V.A., V.A1, V.A1b manufactured by C. W. Brabender Instruments, Inc., Hackensack, N.J. and designed to operate at 75 RPM) having a 700 cm.-gm. sensitivity cartridge. The dispersion is heated at the rapid setting from ambient temperature to 95° C. and held at 95° C. until the peak viscosity is reached. Holding is continued for 10 more minutes after the peak has been reached. The viscosity readings in Brabender units (B.U.) are recorded at peak viscosity and at peak viscosity plus 10 minutes. The difference between the peak viscosity and the final viscosity is the acid viscosity breakdown. If however, no peak viscosity is reached within one hour, then the starch is considered to have a zero breakdown and therefore falls within the required range of 400 B.U. or less.

This breakdown is correlated to the modified starch disintegrant's performance in the tablet, and it is used to distinguish between sufficiently crosslinked, pregelatinized starches and insufficiently crosslinked, pregelatinized starches. Highly crosslinked starches show low swelling in cold water and little or no acid viscosity breakdown and therefore superior disintegration times. Unmodified or lightly crosslinked starches show more swelling in cold water, a large acid viscosity breakdown, and therefore poor disintegration times.

The modified starch powders suitable for tablet disintegrants and those not suitable for tablet disintegrants can not be adequately distinguished by a standard (i.e. non-acid) Brabender procedure.

C. RELATIONSHIP BETWEEN SWELLING AND ACID VISCOSITY BREAKDOWN

The following table shows the relationship between the swelling values and acid viscosity breakdown, as determined by the above procedures, for various starch bases which have been crosslinked and pregelatinized and compares the values with those for pregelatinized starch bases which have not been crosslinked.

| Starch | | Crosslinking Reagent | Swelling (mls.) | Acid Viscosity Breakdown (B.U.) |
|---|---|---|---|---|
| Pregel.[a] | corn starch | — | 13 | 695 |
| Pregel. | corn starch | 0.25% STMP[b] | 10 | 350 |
| Pregel. | corn starch | 0.50% STMP | 9 | 143 |
| Pregel. | corn starch | 0.75% STMP | 8 | 40 |
| Pregel. | corn starch | 1.50% Epi[c] | 4 | 0 |
| Pregel. | potato starch | — | 100 | 1790 |
| Pregel. | potato starch | 0.02% Epi | 25 | 560 |
| Pregel. | potato starch | 0.06% Epi | 17 | 150 |
| Pregel. | potato starch | 0.15% Epi | 8 | 0 |
| Pregel. | waxy corn starch | — | 100 | 1460 |
| Pregel. | waxy corn starch | 0.05% POCl$_3$[d] | 25 | 1280 |
| Pregel. | waxy corn starch | 0.10% POCl$_3$ | 18 | 370 |
| Pregel. | waxy corn starch | 0.40% POCl$_3$ | 10 | 0 |
| Pregel. | tapioca starch | — | 100 | 520 |
| Pregel. | tapioca starch | 0.025% POCl$_3$ | 10 | 320 |
| Pregel. | tapioca starch | 0.100% POCl$_3$ | 7 | 20 |

[a]Abbreviation for pregelatinized
[b]Sodium trimetaphosphate
[c]Epichlorohydrin
[d]Phosphorus oxychloride It should be noted that pregelatinized corn starch which has not been crosslinked has a swelling value of 13 ml. which is below the maximum value of 25 ml.; however, it has an acid viscosity breakdown of 695 B.U. which is above the required range of 400 B.U. or less. Therefore, suitable modified starch powders must be characterized by both the required swelling value and breakdown.

D. TABLET PREPARATION AND EVALUATION

All of the tablets were made using a Stokes B-2, 16 station rotary tablet press equipped with ⅜ in. standard concave punches. Tablet weight was determined by averaging the readings of ten tablets weighed on an appropriate balance. A Delamar PT-1000 hydraulic tablet hardness tester was used to determine tablet strength by averaging the readings of ten tablets. Disintegration times were determined according to method <701> for uncoated tablets using water at 37°±2° C. as the medium (see U.S. Pharmacopeia National Formulary, USP XX, NF XV p. 958, 1980). The starches used as disintegrants, including those of this invention and the comparative starches used in the following examples, all had a comparable particle size.

EXAMPLE I

This example describes the preparation of several crosslinked, pregelatinized corn starch powders for use as disintegrants and their evaluation in an insoluble, direct compression tabletting formulation. It also compares their performance with that of crosslinked corn starch, pregelatinized corn starch, unmodified native corn starch, and a carboxymethyl potato starch disintegrant, a well-known tablet disintegrant widely used in the pharmaceutical industry.

Starch disintegrants I-A to I-C were prepared by crosslinking the starch with phosphorus oxychloride and then pregelatinizing a slurry of the crosslinked starch by drum drying. A total of 100 parts of corn starch was suspended in 150 parts of water and the pH adjusted to about 11.5 with dilute sodium hydroxide. The indicated amounts of phosphorus oxychloride were then added. The mixture was reacted for 1-2 hr. at room temperature, neutralized to pH 5.5 with dilute hydrochloric acid, and filtered. The resulting crosslinked starch was washed and dried. A total of 100 parts of the starch was then suspended in 150 parts of water and, if necessary, the pH was adjusted to 5.5-6.5 with either dilute sodium hydroxide or dilute hydrochloric acid. The starch slurry was then drum dried at a drum surface temperature of about 150° C. (302° F.). The resulting sheet of crosslinked, pregelatinized starch was finely pulverized using a Raymond hammer mill. The modified starch powders were characterized by their low swelling in cold water and acid viscosity breakdown using the procedures previously described.

The tabletting formulation, an insoluble formulation hereafter designated Direct Compression-I (D.C.-I), was prepared by dry blending a mixture of 94.5 parts Emcompress (trade name for a dicalcium phosphate dihydrate binder supplied by Edward Mendell Co.), 0.5 part magnesium stearate (lubricant), and 5 parts starch and directly compressing the dry blend into tablets using the procedure and equipment previously described. The tablets were evaluated for their hardness and disintegration time. The results are given in Table I.

The results show that the crosslinked, pregelatinized starch powders were superior as disintegrants to the unmodified native corn starch and to the pregelatinized corn starch, the latter confirming that pregelatinization alone will not provide a starch with satisfactory disintegration performance. It also shows that the more highly crosslinked, lower swelling starch (I-C), which showed the lowest breakdown and swelling value of the modified starches, had the best disintegration time. In addition, the results confirm that both acid viscosity breakdown and swelling values must be used to characterize suitably modified starches. It is shown that the modified starches which were comparable in performance with carboxymethyl potato starch swell only slightly, whereas carboxymethyl potato starch, which has a breakdown of zero, swells to a much greater degree (50 vs. 8-10 ml.). The rapid and high degree of swelling characteristic of carboxymethyl potato starch may be undesirable especially when the disintegrant comes in contact with water before the tablet is formed.

TABLE I

| Starch and Treatment | Disintegrant | | Tablets (Formulation - Direct Compression-I) | | |
|---|---|---|---|---|---|
| | Acid Viscosity Breakdown (B.U.) | Swelling (ml.) | Average Weight (mg.) | Average Hardness (kg./cm.$^2$) | Average Disintegration Time (sec.) |
| Pregelatinized corn starch crosslinked w/0.06% POCl$_3$ (I-A) | 338 | 10 | 506 | 8.3 | 35 |
| Pregelatinized corn starch crosslinked w/0.09% POCl$_3$ (I-B) | 175 | 9 | 508 | 9.0 | 31 |
| Pregelatinized corn starch crosslinked w/0.12% POCl$_3$ (I-C) | 30 | 8 | 506 | 8.1 | 26 |
| Pregelatinized corn starch (comparative) | 695 | 13 | 505 | 8.4 | 86 |
| Unmodified native corn starch (comparative) | 640 | 1.5 | 495 | 8.2 | 120–240 |
| Carboxymethyl potato starch (comparative) | 0 | 50 | 512 | 8.9 | 29 |
| No starch (blank) | — | — | 500 | 8.5 | Did not disintegrate |

EXAMPLE II

This example describes the preparation of additional crosslinked, pregelatinized corn starch and potato starch powders prepared using varying amounts of sodium trimetaphosphate and epichlorohydrin as the crosslinking agents. The powders were evaluated as disintegrants at the same level in the formulation designated D.C.-I (described in Example I).

Starch disintegrants II-A to II-D were prepared by crosslinking corn starch with the indicated amount of sodium trimetaphosphate (STMP) and then pregelatinizing a slurry of the crosslinked starch using the drum drying procedure of Example I, as well as the pulverizing procedure therein. The crosslinking was carried out as in Example I except that the reaction time was 6–8 hrs.

Starch disintegrants II-E to II-H were prepared by crosslinking potato starch in a similar manner using the indicated amounts of epichlorohydrin (Epi) except that the reaction was carried out for 16 hr. at 37° C. Pregelatinization and pulverizing were carried out as before. The preparation, characterization, and evaluation of the disintegrants is summarized in Table II.

The results show that crosslinked, pregelatinized starch powders useful as disintegrants can be prepared using crosslinking agents other than phosphorus oxychloride and that, again, the more highly crosslinked starches, as characterized by their lower acid viscosity breakdown values and lower swelling in cold water, were the most effective disintegrants.

EXAMPLE III

This example compares the disintegration performance of the pulverized, crosslinked, drum dried corn starch powders of this invention with that of two corn starch samples which were crosslinked, dried, and pulverized, but not pregelatinized (i.e. drum dried).

TABLE II

| Starch and Treatment | Disintegrant | | Tablets (Formulation - Direct Compression-I) | | |
|---|---|---|---|---|---|
| | Acid Viscosity Breakdown (B.U.) | Swelling (ml.) | Average Weight (mg.) | Average Hardness (kg/cm$^2$) | Average Disintegration Time |
| Pregelatinized corn starch crosslinked w/0.250% STMP (II-A) | 350 | 10 | 497 | 8.0 | 60 sec. |
| Pregelatinized corn starch crosslinked w/0.500% STMP (II-B) | 143 | 9 | 504 | 8.1 | 44 sec. |
| Pregelatinized corn starch crosslinked w/0.625% STMP (II-C) | 98 | 9 | 510 | 8.2 | 34 sec. |
| Pregelatinized corn starch crosslinked w/0.750% STMP (II-D) | 40 | 8 | 503 | 8.2 | 30 sec. |
| Pregelatinized corn starch (comparative) | 695 | 13 | 505 | 8.4 | 86 sec. |
| Pregelatinized potato starch crosslinked w/0.02% Epi (II-E) | 560 | 25 | 531 | 8.4 | >30 min. |
| Pregelatinized potato starch crosslinked w/0.06% Epi (II-F) | 150 | 17 | 535 | 8.3 | 62 sec. |
| Pregelatinized potato starch crosslinked w/0.10% Epi (II-G) | 40 | 10 | 537 | 8.2 | 27 sec. |
| Pregelatinized potato starch crosslinked w/0.15% Epi (II-H) | 0 | 8 | 534 | 8.2 | 21 sec. |
| Pregelatinized potato starch (comparative) | 1790 | 100 | 530 | 8.6 | Did not disintegrate |

The results, which are given in Table III, show that the crosslinked non-pregelatinized starches performed essentially the same as unmodified native corn starch and therefore were inferior to the crosslinked pregelatinized starch powders. While the non-pregelatinized starch crosslinked with 0.06% phosphorus oxychloride did fall outside the acid viscosity breakdown range, the non-pregelatinized starch crosslinked with 0.12% phosphorus oxychloride, which had a breakdown of 280 B.U., fell within the required range for satisfactory performance. However, the non-pregelatinized crosslinked starches do not swell to any significant degree and their performance as disintegrants was therefore poor. This can be seen from the comparatively very low swelling values (1.4 ml. which is below the required value of above 3 ml.).

EXAMPLE IV

This example shows the use of two different crosslinked, pregelatinized corn starch powders in a direct compression formulation containing a mixture of soluble and insoluble binders. The disintegration performance of the starches was compared with that of unmodified native corn starch, pregelatinized corn starch, carboxymethyl potato starch, and Starch 1500 (trade name for a commercially available, physically compacted starch binder-disintegrant marketed by The Colorcon Corp.).

Starch disintegrant IV-A was prepared as in Example I using phosphorus oxychloride as the crosslinking agent. Starch disintegrant IV-B was prepared as in Example II using sodium trimetaphosphate as the crosslinking agent. The tabletting formulation, hereafter designated as D.C.-II, was prepared as in Example I except that the dry blend contained 47.5 parts Emcompress, 47.5 parts Emdex (tradename for a spray crystallized maltose-dextrose supplied by the E. Mendell Co.), 1 part magnesium stearate, and 4 parts starch.

latinized non-crosslinked corn starch, and far better than unmodified native corn starch. The crosslinked, pregelatinized corn starch powder was also significantly better than Starch 1500, although the latter was better than the unmodified native corn starch. Starch 1500 had an acid viscosity breakdown of 140 B.U. and a swelling value of 6 ml., both within the range required for crosslinked, pregelatinized starch powders which are satisfactory as disintegrants. However, a microscopic examination of an aqueous dispersion of Starch 1500 explained the performance difference. This compacted starch was made up of a mixture of birefringent and non-birefringent granules, with the birefringent granules largely resembling those of unmodified native corn starch, as well as some aggregates of birefringent and non-birefringent granules and some fragments. A microscopic examination of an aqueous dispersion of the crosslinked, pregelatinized starch powders of this invention showed that they were virtually free of birefringent granules and were uniformly and partially swollen.

EXAMPLE V

This example shows the preparation of crosslinked, pregelatinized starch powders for use as disintegrants using starch bases other than regular corn starch and their evaluation as disintegrants in both types of direct compression formulations—D.C.-I containing the insol-

TABLE III

| Disintegrant | | | Tablets (Formulation - Direct Compression-I) | | |
|---|---|---|---|---|---|
| Starch and Treatment | Acid Viscosity Breakdown (B.U.) | Swelling (ml.) | Average Weight (mg.) | Average Hardness (kg./cm.$^2$) | Average Disintegration Time |
| Pregelatinized corn starch crosslinked w/0.06% POCl$_3$ | 338 | 10 | 506 | 8.3 | 35 sec. |
| Pregelatinized corn starch crosslinked w/0.12% POCl$_3$ | 30 | 8 | 506 | 8.1 | 26 sec. |
| Corn starch crosslinked w/0.06% POCl$_3$ (comparative) | 520 | 1.4 | 513 | 9.1 | 3.5 min. |
| Corn starch crosslinked w/0.12% POCl$_3$ (comparative) | 280 | 1.4 | 508 | 9.0 | 4 min. |
| Unmodified native corn starch (comparative) | 640 | 1.5 | 516 | 9.0 | 2–4 min. |

The tablets were compressed and evaluated as before; the results are given in Table IV.

uble binder and D.C.-II containing the soluble/insoluble binder mixture.

TABLE IV

| Disintegrant | | | Tablets (Formulation - Direct Compression-II) | | |
|---|---|---|---|---|---|
| Starch and Treatment | Acid Viscosity Breakdown (B.U.) | Swelling (ml.) | Average Weight (mg.) | Average Hardness (kg./cm.$^2$) | Average Disintegration Time |
| Pregelatinized corn starch crosslinked w/0.04% POCl$_3$ (III-A) | 80 | 9 | 604 | 8.2 | 9.0 |
| Pregelatinized corn starch crosslinked w/0.50% STMP (III-B) | 0 | 8 | 574 | 9.6 | 9.5 |
| Pregelatinized corn starch (comparative) | 695 | 13 | 573 | 9.2 | 18.0 |
| Unmodified native corn starch (comparative) | 640 | 1.5 | 588 | 9.8 | 60.0 |
| Carboxymethyl potato starch (comparative) | 0 | 50 | 602 | 8.5 | 9.5 |
| Starch 1500 (comparative) | 140 | 6 | 582 | 9.6 | 28.0 |
| No starch (blank) | — | — | 573 | 9.6 | Did not disintegrate |

The results show that, even though it takes much longer for this direct compression formulation containing the soluble binder to disintegrate, the crosslinked, pregelatinized starch powders were comparable to carboxymethyl potato starch, much better than the prege- The crosslinking, pregelatinizing, and pulverizing methods previously described were used. The results are given in Table V (for comparison, additional crosslinked, pregelatinized corn starch powders were prepared and evaluated and these are included in the table as references).

The results show that other starch bases can be used provided the crosslinking and pregelatinization give a starch powder having the required low acid viscosity breakdown of about 400 B.U., or preferably less, and the required swelling value of below 25 ml., preferably 18 ml. or less. The waxy corn starch powder (V-D) which had the same breakdown (i.e. 0) as the reference powder (10 min. and 9 min. vs. 9 min.) in the D.C.-II tabletting formulation.

EXAMPLE VI

This example shows the use of a crosslinked, pregelatinized corn starch powder as a disintegrant in a wet granulation tabletting formulation. The disintegrant's performance, when added both intragranularly and extragranularly, was compared with that of unmodified native corn starch and carboxymethyl potato starch.

TABLE V

| Disintegrant Starch and Treatment | Acid Viscosity Breakdown (B.U.) | Swelling (ml.) | Avg. Weight (mg.) | Avg. Hardness (kg./cm.$^2$) | Avg. Disintegration Time |
|---|---|---|---|---|---|
| *Tablets (Formulation - Direct Compression-I)* | | | | | |
| Pregelatinized waxy corn starch crosslinked w/0.05% POCl$_3$ (V-A) | 1280 | 25 | 565 | 9.3 | 3 min. 35 sec. |
| Pregelatinized waxy corn starch crosslinked w/0.10% POCl$_3$ (V-B) | 370 | 18 | 566 | 9.3 | 1 min. 11 sec. |
| Pregelatinized waxy corn starch crosslinked w/0.20% POCl$_3$ (V-C) | 20 | 17 | 559 | 8.6 | 43 sec. |
| Pregelatinized waxy corn starch crosslinked w/0.40% POCl$_3$ (V-D) | 0 | 10 | 555 | 9.1 | 28 sec. |
| Pregelatinized waxy corn starch (comparative) | 1460 | 100 | 572 | 9.3 | Did not disintegrate |
| *Tablets (Formulation - Direct Compression-II)* | | | | | |
| Pregelatinized tapioca starch crosslinked w/0.025% POCl$_3$ (V-E) | 320 | 10 | 541 | 9.1 | 16 min. |
| Pregelatinized tapioca starch crosslinked w/0.050% POCl$_3$ (V-F) | 110 | 9 | 560 | 9.8 | 13 min. |
| Pregelatinized tapioca starch crosslinked w/0.200% POCl$_3$ (V-G) | 0 | 6 | 555 | 9.8 | 10 min. |
| Pregelatinized tapioca starch (comparative) | 520 | 100 | 555 | 9.2 | 90 min. |
| *Tablets (Formulation - Direct Compression-II)* | | | | | |
| Pregelatinized potato starch crosslinked w/0.025% POCl$_3$ (V-H) | 590 | 28 | 546 | 9.8 | 18 min. |
| Pregelatinized potato starch crosslinked w/0.050% POCl$_3$ (V-I) | 350 | 15 | 545 | 9.7 | 14 min. |
| Pregelatinized potato starch crosslinked w/0.100% POCl$_3$ (V-J) | 70 | 10 | 551 | 9.9 | 9 min. |
| Pregelatinized potato starch (comparative) | 1790 | 100 | 545 | 9.8 | 225 min. |
| *Tablets (Formulation - Direct Compression-I)* | | | | | |
| Pregelatinized corn starch crosslinked w/0.50% STMP (reference) | 0 | 8 | 565 | 8.2 | 27 sec. |
| *Tablets (Formulation - Direct Compression-II)* | | | | | |
| Pregelatinized corn starch crosslinked w/0.50% STMP (reference) | 0 | 8 | 574 | 9.6 | 9 min. |
| No starch (blank) | — | — | 573 | 9.6 | Did not disintegrate | corn starch powder, but a somewhat higher swelling value (10 vs. 8 ml.), had a comparable disintegration time (28 vs. 27 sec.) in the D.C.-I tabletting formulation. The waxy corn starch powder (V-A) having an acid viscosity breakdown and swelling value above the maximum permitted levels (400 B.U. and 25 ml.) took much longer to to disintegrate and was not satisfactory as a disintegrant. Crosslinked, pregelatinized starch powders based on tapioca and potato starch which had the preferred low acid viscosity breakdowns (70 and 0 B.U.) and low swelling values (10 and 6 ml.) had disintegration times comparable to the reference corn starch The tablesetting formulation was prepared by dry blending a mixture of diluents, incorporating the binder which was added either as a dry powder or dissolved in water, mixing in 7-8% water by weight (based on the total dry powder weight) to wet and granulate the particles, drying the mixture, and grinding it to a flowable powder (usually 10-40 mesh in particle size). The mixture contained 31.50 parts crystalline lactose, 15.75 parts calcium sulfate, 31.50 parts dicalcium phosphate, and 15.75 parts powdered sugar. A total of 5 parts of the indicated starches were added both prior to and after granulation. The lubricant, 0.50 part magnesium stearate, was added just before tabletting. The results are given in Table VI.

TABLE VI

| Starch and Treatment | Tablet (Formulation - Wet Granulation) | | | | | |
|---|---|---|---|---|---|---|
| | Intragranular Addition | | | Extragranular Addition | | |
| | Average Weight (mg.) | Average Hardness (kg./cm.$^2$) | Average Disintegration Time (min.) | Average Weight (mg.) | Average Hardness (kg./cm.$^2$) | Average Disintegration Time (min.) |
| Pregelatinized corn starch crosslinked with 0.1% POCl$_3$ | 527 | 11.6 | 18 | 524 | 5.7 | 7 |
| Unmodified native corn starch (comparative) | 493 | 6.2 | 34 | 555 | 7.0 | 23 |
| Carboxymethyl potato starch (comparative) | 542 | 11.1 | 23 | 548 | 5.9 | 11 |
| No starch (blank) | 559 | 11.4 | 50 | 559 | 11.4 | 50 |

The results show that the crosslinked, pregelatinized corn starch powder was very effective in the wet granulation formulation regardless of how it was added and that it was much more effective than unmodified native corn starch and even superior to carboxymethyl potato starch. It is believed that carboxymethyl potato starch swells prematurely when the formulation is wetted for granulation before the tablet is formed.

EXAMPLE VII

This example illustrates the use of the crosslinked, pregelatinized corn starch powder at lower usage levels and compares its disintegration performance with that of unmodified native corn starch, carboxymethyl potato starch, and Starch 1500. The tabletting formulation was the same as formulation D.C. II of Example IV except that U.S.P. lactose was used in place of Emdex. The results are given in Table VII (for reference, data on its usage at 5.0% by weight is included in the table).

The results show that the disintegration time dropped as the level of disintegrant decreased. They further show that at any usage level the crosslinked, pregelatinized corn starch powder was vastly superior to unmodified native corn starch, much more effective than Starch 1500, and in general comparable to carboxymethyl potato starch.

EXAMPLE VIII

This example describes the simultaneous crosslinking and pregelatinization of corn starch. A total of 100 parts of corn starch is suspended in 150 parts of water containing 0.5 part dissolved sodium chloride; the pH is adjusted to 8 with dilute sodium hydroxide solution and 1 part sodium trimetaphosphate is added. The starch slurry is then drum dried and pulverized as in Example I. The modified starch powder should have disintegration properties comparable to those of powders prepared using separate crosslinking and pregelatinization steps.

TABLE VII

| Starch and Treatment | Tablets (Formulation - Direct Compression-II) Average Disintegration Time | | |
|---|---|---|---|
| | 1.5% Disintegrant | 3.0% Disintegrant | 5.0% Disintegrant |
| Pregelatinized corn starch crosslinked with 0.50% STMP | 67 sec. | 43 sec. | 44 sec. |
| Unmodified native corn starch (comparative) | >1 hr. | 30 min. | 139 sec. |
| Starch 1500 (comparative) | 173 sec. | 73 sec. | 53 sec. |
| Carboxymethyl potato starch (comparative) | 37 sec. | 33 sec. | 34 sec. |
| No starch (blank) | Did not disintegrate | Did not disintegrate | Did not disintegrate |

EXAMPLE IX

This example describes the preparation of tablets containing active ingredients and the modified starch powders herein and compares their disintegration performance with that of the same tablets containing pregelatinized corn starch, unmodified native corn starch, Starch 1500, and carboxymethyl potato starch as disintegrants.

Tablets containing caffeine as the active ingredient were prepared by dry blending 50.00 parts caffeine, 0.33 part stearic acid, 0.33 part magnesium stearate, 4.00 parts starch, and 45.34 parts Emdex. Tablets containing aspirin as the active ingredient were prepared by dry blending 75.00 parts aspirin (U.S.P. 40 mesh crystals marketed by Monsanto Chemical Co.), 0.50 part magnesium stearate, 2.50 parts starch, and 22 parts Emcompress. The dry blends were directly compressed using the tabletting procedure previously described. Blanks were prepared using no disintegrant and sufficient additional binder (Emdex or Emcompress) to give 100 parts. The tablets were evaluated for their hardness and disintegration times; the results are given in Tables VIII and IX.

The results show that the crosslinked, pregelatinized corn starch powder was comparable in both formulations to carboxymethyl potato starch, much better than Starch 1500 or pregelatinized (non-crosslinked) corn starch, and far superior to unmodified native corn starch, which in the aspirin formulation did not disintegrate even after 1.5 hr.

Summarizing, this invention is seen to provide free-flowing modified starch powders which are low swelling in cold water and useful as tablet disintegrants in compressed tablets prepared by any tabletting method containing the modified starch powders.

TABLE VIII

| Disintegrant Starch and Treatment | Tablets (Caffeine Formulation - Direct Compression) | | |
|---|---|---|---|
| | Average Weight (mg.) | Average Hardness (kg./cm.$^2$) | Average Disintegration Time (min.) |
| Pregelatinized corn starch crosslinked w/0.04% POCl$_3$ | 458 | 15.0 | 7 |
| Pregelatinized corn starch (comparative) | 482 | 15.7 | 14 |
| Unmodified native corn starch (comparative) | 473 | 15.5 | 22 |
| Starch 1500 (comparative) | 476 | 15.5 | 16 |
| Carboxymethyl potato starch (comparative) | 461 | 15.8 | 7 |
| No starch (blank) | 469 | 16.0 | 26 |

TABLE IX

| Disintegrant Starch and Treatment | Tablets (Aspirin Formulation - Direct Compression) | | |
|---|---|---|---|
| | Average Weight (mg.) | Average Hardness (kg./cm.$^2$) | Average Disintegration Time |
| Pregelatinized corn starch crosslinked w/0.04% POCl$_3$ | 651 | 7.1 | 2 min. |
| Pregelatinized corn starch (comparative) | 662 | 7.8 | 8 min. |
| Unmodified native corn starch (comparative) | 665 | 7.9 | 1.5 hr. |
| Starch 1500 (comparative) | 663 | 7.8 | 13 min. |
| Carboxymethyl potato starch (comparative) | 652 | 7.8 | 2 min. |
| No starch (blank) | 695 | 7.9 | 1.5 hr. |

Now that the preferred embodiments of the present invention have been described in detail, various modifications and improvements thereon will become readily apparent to those skilled in the art. Accordingly, the sprit and scope of the invention are to be limited only by the appended claims and not by the foregoing specification.

What is claimed is:

1. A disintegrant for compressed tablets, consisting essentially of a free-flowing, crosslinked and pregelatinized, low swelling starch powder having a moisture content of about 12% by weight or less and derived from a cold-water-insoluble, granular starch base; said starch powder characterized by all of the following:
    (a) its uniformly swollen, virtually non-birefringent granules,
    (b) by a cold water swelling value above about 3 and below about 25 ml., and
    (c) by an acid viscosity breakdown of about 400 B.U. or less; said acid viscosity breakdown determined by heating an aqueous dispersion containing 9% of said starch powder and 1% glacial acetic acid, both by weight and based on anhydrous starch, at from ambient temperature to 95° C., holding at 95° C. until a peak viscosity is reached, but for no more than 1 hr. if no peak viscosity is reached, holding for an additional 10 min. at 95° C. after said peak viscosity is reached, and recording a final viscosity at 95° C. plus 10 min., with the difference between said peak viscosity and said final viscosity being said acid viscosity breakdown and with said acid viscosity breakdown considered as zero when no peak viscosity is reached; said measurement being carried out in a Brabender Visco/Amylo/Graph having a 700 cm.-gm. sensitivity cartridge; said starch powder effectively disintegrating said tablet when placed in a fluid.

2. The disintegrant of claim 1, wherein said starch base is corn starch, waxy corn starch, potato starch, or tapioca starch and said starch powder has the moisture content of about 6-10% by weight or less and the cold water swelling value of about 4-18 ml.

3. The disintegrant of claim 2, wherein said starch base is corn starch and said starch powder has a cold water swelling value of about 4 to 12 ml.

4. The disintegrant of claim 3, wherein said starch powder is characterized by an acid viscosity breakdown of 150 B.U. or less and a swelling vaue of 10 ml. or less.

5. The method for preparing the disintegrant of claim 1, which comprises the steps of:
    (a) crosslinking and pregelatinizing a cold-water-insoluble, granular starch base in the presence of water;
    (b) drying said crosslinked and pregelatinized starch, if necessary, to said moisture content of about 12% by weight or less; and
    (c) finely pulverizing said crosslinked and pregelatinized starch to said low swelling starch powder having a particle size suitable for tabletting.

6. The method of claim 5, wherein said crosslinking is carried out with phosphorous oxychloride or sodium trimetaphosphate and wherein said pregelatinization and drying are carried out by drum drying an aqueous slurry of said crosslinked starch.

7. The method of claim 5, wherein said starch base is simultaneously crosslinked, pregelatinized, and drum dried.

8. A non-friable, hard compressed tablet comprising a tabletting mixture of an active ingredient, a binder, and a disintegrant, characterized in that said disintegrant consists essentially of a free-flowing, crosslinked and pregelatinized, low swelling starch powder having a moisture content of about 12% by weight or less and derived from a cold-water-insoluble, granular starch base; said starch powder characterized by all of the following:
    (a) its uniformly swollen virtually non-birefringent granules,
    (b) a cold water swelling value above about 3 and below about 25 ml., and
    (c) an acid viscosity breakdown of about 400 B.U. or less; said acid viscosity breakdown determined by heating an aqueous dispersion containing 9% of said modified starch powder and 1% glacial acetic acid, both by weight and based on anhydrous starch, at from ambient temperature to 95° C., holding at 95° C. until a peak viscosity is reached, but for no more than 1 hr. if no peak viscosity is reached, holding for an additional 10 min. at 95° C. when said peak viscosity is reached, and recording a final viscosity at 95° C. plus 10 min., with the difference between said peak viscosity and said final viscosity being said acid viscosity breakdown and with said acid viscosity breakdown considered as zero when no peak viscosity is reached; said measurement being carried out in a Brabender/Visco/Amylo/Graph having a 700 cm.-gm. sensitivity cartridge.

9. The table of claim 8, wherein said starch powder is derived from corn starch, waxy corn starch, potato starch, or tapioca starch crosslinked by treatment with phosphorus oxychloride or sodium trimetaphosphate and drum dried, said starch powder having the moisture content of about 6–10% by weight or less, the swelling value of 10 ml. or less, and the breakdown of 150 B.U. or less.

10. The tablet of claim 8, wherein said disintegrant is present in an amount of 10% by weight or less, based on the total weight of said tabletting mixture.

11. In a method for preparing compressed tablets, the step which comprises adding, as a disintegrant to a tabletting mixture at any time prior to compression thereof, a free-flowing, crosslinked and pregelatinized, low swelling starch powder having a moisture content of about 12% by weight or less and derived from a cold water insoluble, granular starch base; said starch powder characterized by all of the following:

(a) its uniformly swollen, virtually non-birefringent granules;
(b) a cold water swelling value of above about 3 and below about 25 ml., and
(c) an acid viscosity breakdown of 400 B.U. or less; said acid viscosity breakdown determined by heating an aqueous dispersion containing 9% of said modified starch powder and 1% glacial acetic acid, both by weight and based on anhydrous starch, at from ambient temperature to 95° C., holding at 95° C. until a peak viscosity is reached, but for no more than 1 hr. if no peak viscosity is reached, holding for an additional 10 min. at 95° C. after said peak viscosity is reached, and recording a final viscosity at 95° plus 10 min., with the difference between said peak viscosity and said final viscosity being said acid viscosity breakdown and with said acid viscosity breakdown considered as zero when no peak viscosity is reached; said measurement being carried out in a Brabender Visco/Amylo/Graph having a 700 cm.-gm. sensitivity cartridge.

12. The method of claim 11, wherein said starch powder is added in an amount of 10% by weight or less, based on the total weight of said tabletting mixture.

* * * * *